United States Patent [19]

Matossian et al.

[11] Patent Number: 5,303,574
[45] Date of Patent: Apr. 19, 1994

[54] EVALUATION OF THE EXTENT OF WEAR OF ARTICLES

[75] Inventors: Jesse N. Matossian, Woodland Hills, Calif.; Paul H. Mikkola, Saint Charles, Mich.; John L. Bartelt, Camarillo, Calif.

[73] Assignees: Hughes Aircraft Company, Los Angeles, Calif.; General Motors Corp., Detroit, Mich.

[21] Appl. No.: 988,397

[22] Filed: Dec. 9, 1992

Related U.S. Application Data

[63] Continuation of Ser. No. 654,865, Feb. 12, 1991, abandoned.

[51] Int. Cl.$^5$ .............................................. G01N 3/56
[52] U.S. Cl. ....................... 73/7; 83/522.27; 356/402; 356/448; 428/543; 428/908.8
[58] Field of Search ................ 73/7, 8, 104, 150 R; 356/402, 408, 421, 422, 423, 445, 448; 81/488; 83/522.27; 427/8, 523-531, 249; 428/543, 688, 908.8, 934, 935, 936, 938

[56] References Cited

U.S. PATENT DOCUMENTS

| | | | |
|---|---|---|---|
| 3,476,482 | 11/1969 | Howard et al. | 356/448 X |
| 3,483,385 | 12/1969 | Heoslip et al. | 356/448 X |
| 3,660,815 | 5/1972 | Rees | 73/7 X |
| 3,900,636 | 8/1975 | Curry et al. | 427/38 |
| 4,554,853 | 11/1985 | Nitschmann et al. | 83/522.27 |
| 4,680,281 | 10/1986 | Thompson et al. | 340/680 X |
| 4,789,703 | 12/1988 | Fabris et al. | 73/7 UX |
| 4,886,009 | 12/1989 | Gondar et al. | 116/208 |
| 4,913,881 | 4/1990 | Evess | 356/402 X |
| 5,056,353 | 10/1991 | Matano | 73/7 |
| 5,074,983 | 12/1991 | Eltoukhy et al. | 73/7 X |
| 5,130,161 | 7/1992 | Mansur et al. | 427/38 X |
| 5,143,747 | 9/1992 | Matossian et al. | 427/38 |

FOREIGN PATENT DOCUMENTS

| | | | |
|---|---|---|---|
| 0303202 | 2/1989 | European Pat. Off. | |
| 253678 | 3/1983 | Fed. Rep. of Germany | |
| 2248487 | 5/1975 | France | |
| 177243 | 9/1985 | Japan | 73/8 |
| 191037 | 8/1989 | Japan | |
| 338820 | 6/1972 | U.S.S.R. | 73/8 |
| 486243 | 12/1975 | U.S.S.R. | 73/8 |
| 1546891 | 2/1990 | U.S.S.R. | 73/7 |
| 1596228 | 9/1990 | U.S.S.R. | 73/7 |

OTHER PUBLICATIONS

J. Musil et al., "Ion-Assisted Sputtering of TiN Films", *Surface and Coatings Technology*, vol. 43/44, pp. 259–269 (1990).

I. Takano, et al., "Effect of $N_2^+$ Ion Dose on the Hardness and Other properties of AIN Thin Films Prepared by the Dynamic Mixing Method", Nuc. Inst. and Methods in Phys. Research B37/38 (1989) pp. 688–691.

S. Lucas et al., "Temperature and Dose Dependences of Nitrogen Implantation Into Aluminium", Nuc. Instruments and Methods in Phys. Research B50 (1990), pp. 401–405.

(List continued on next page.)

*Primary Examiner*—Tom Noland
*Attorney, Agent, or Firm*—Vijayalakshmi D. Duraiswamy; Wanda K. Denson-Low

[57] ABSTRACT

An article (40), such as a piece of manufacturing tooling, is modified prior to use by treating a portion of its surface (38) to be worn so that the treated surface worn more than a preselected amount has a different appearance than the treated surface worn less than the preselected amount, using a treatment process in which the treated surface is at least as wear resistant as the untreated surface. In one approach, the surface (38) is treated by implanting ions to a preselected depth. The ions are chosen so that the substrate has a different color at depths less than the preselected depth than does the substrate at depths greater than the preselected depth. After wear, the treated surface is visually inspected for color variations that indicate wear to more than the preselected depth. The surface treatment can also be accomplished by ion implanting or ion beam mixing a previously deposited surface coating.

20 Claims, 2 Drawing Sheets

OTHER PUBLICATIONS

Y. Okabe et al., "Coloring of Iron Surface Controled by Ti+-O+ Double-Ion Implantations"Nuc. Inst. and Methods in Phys. Research B7/8 (1985) pp. 184-187.

P. B. Madakson, "Surface Stresses and the Hardness of Ion Implanted Aluminium", J. Phys. D: Appl. Phys. vol. 18, pp. 531-540 (1985).

T. Venkatesan, "High Energy Ion Beam Modification of Polymer Films", Nuc. Inst. and Methods in Physics Research, vol. B7/8 (1985), pp. 461-467.

S. Ohira et al., "Characterization of the Aluminum Surface Layer Implanted with Nitrogen", Mat. Sci. and Eng., vol. 90, pp. 143-148 (1987).

Y. Wang, et al., "The Modification of the Mechanical Properties of Soft Metals by Ion Implantation", Vacuum, vol. 39, Nos. 2-4, pp. 293-295 (1989).

V. K. Galaev et al. "Rapid Testing of Wear During Reciprocating Motion"; *Ind. Lab.* (*USA*), vol. 38, No. 1. (Jan. 1972) pp. 132-133.

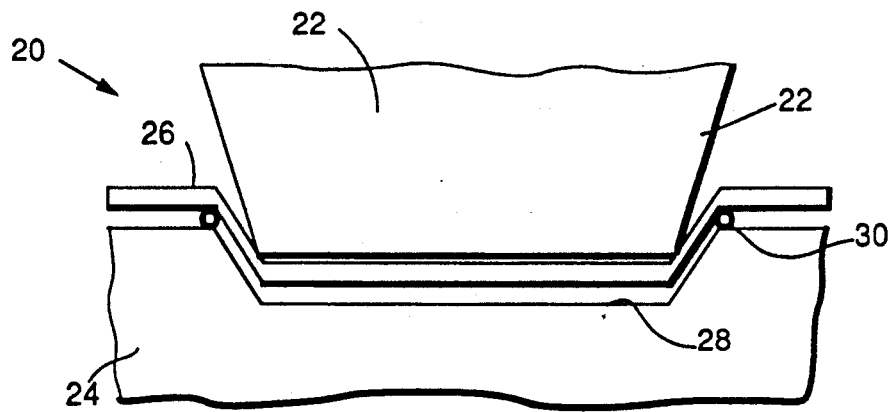
FIG. 1.
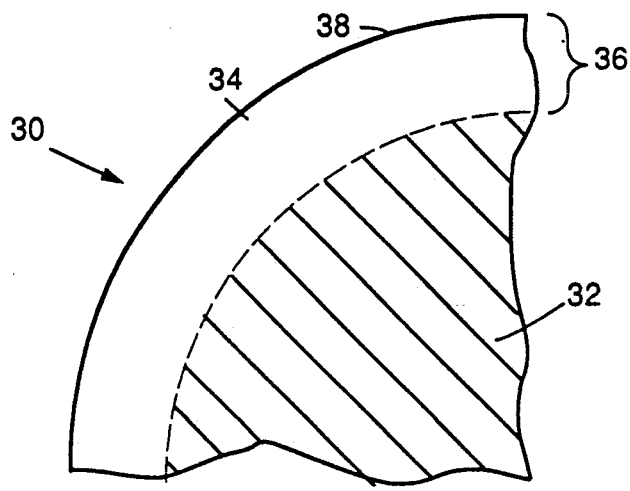
FIG. 2.
FIG. 3.
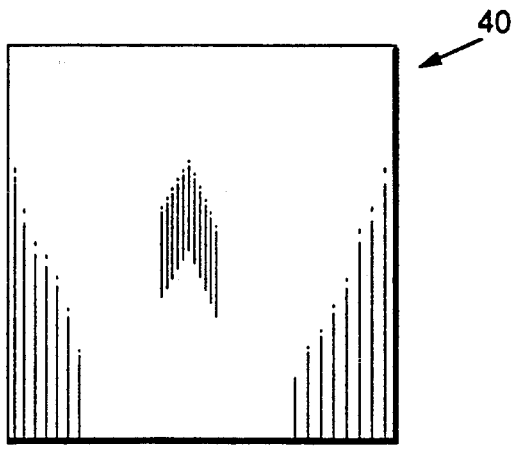

EVALUATION OF THE EXTENT OF WEAR OF ARTICLES

This is a continuation of application Ser. No. 07/654,865, filed Feb. 12, 1991 and now abandoned.

BACKGROUND OF THE INVENTION

This invention relates to the wear of articles, and articles such as those used in manufacturing tooling, and, more particularly, to the evaluation of the extent of wear of such articles without the use of instruments.

Many metallic articles are formed to their final shapes and sizes by metal working techniques utilizing tooling to aid in the forming. In one such technique, a thin metal article is formed from a sheet or coiled strip metal workpiece using a metal forming die. The die is another piece of material having a preselected shape that aids in the forming of the workpiece into its intermediate or final shape. Sheet workpieces are commonly formed by forcing the sheet into a female die using a male die.

Some of the die forming operations involve large tonnages of metal workpieces and produce familiar products. For example, most automobiles have metallic body panels. To fabricate those panels, flat pieces of metal sheet are formed by placing the starting sheet over a female die, and then forcing the sheet into the female die with an appropriately shaped male die. The resulting part has the complex shape of the body panel.

The useful life of tooling such as dies is normally limited by wear that causes changes in their dimensions and thence to the dimensions of the finished parts. As each part is formed, the frictional contact between the sheet workpiece and the tool removes some small amount of material from the tool. Eventually, the tool is so changed in dimension that the final products do not meet the standards. At that point the tool must either be discarded or refurbished.

Evaluation of the extent of wear of tooling is usually accomplished by periodically measuring the dimensions of either the finished part or of the tool itself. It is normally not practical to measure every finished part and/or to measure the tooling after each part is formed, because the measurements would slow the production operation too greatly. For example, if a contoured automobile body panel having a surface area of on the order of 10 square feet is formed between dies, hundreds of dimensional measurements might be required to check whether each dimension of the part is within tolerance as the part emerges from the forming press. Similarly, hundreds of measurements could be required to check the dies to be certain that they are within tolerance.

Another approach is to check the dimensions of the part and/or the tooling periodically, and that is the approach normally taken. If, for example, at one measurement of a formed part all dimensions are within tolerance, then perhaps another ten thousand parts might be formed prior to again measuring the article or the tooling. If at the next measurement there is an unacceptable dimensional variation, then the parts produced since the last inspection would be individually inspected and those not meeting tolerances would be discarded. This procedure can result in scrapping substantial numbers of parts in the event that the loss of tolerances occurred soon after the prior inspection.

In those instances where the tooling itself is to be measured, the measurement process may be slow and cumbersome. The dimensions are typically measured using a micrometer or an automated coordinate-measuring machine. As an example of the time involved, about 6 hours is required to check all of the dimensions of an automobile engine manifold tooling set. The inspection is scheduled after every 10,000 parts formed. From these measurements, retention of dimensions and patterns of wear are evaluated. If the dimensions are no longer within tolerances, then the tooling must be discarded or refurbished.

There is a need for a better approach to evaluation of the extent of tool wear. Desirably, such an approach would be faster, less expensive, and therefore capable of practice more often than existing techniques. The present invention fulfills this need, and further provides related advantages.

SUMMARY OF THE INVENTION

The present invention provides a process for measuring the extent of wear of articles by visual inspection. Such articles can include tooling, articles formed by tooling, or anything else that is subjected to wear. An evaluation of the extent of wear of the article can be performed with a quick visual scan of the article, without making individual measurements. The accuracy of the procedure is as good as other methods.

In accordance with the invention, a process for evaluating the extent of wear of a selected article comprises the steps of furnishing a substrate in the shape of the selected article and having an untreated working surface; treating at least a portion of the untreated working surface of the substrate so that the appearance of the treated surface after wear of more than a preselected amount is altered as compared with the appearance of the treated surface that is not worn by more than the preselected amount, the treated surface being at least as wear resistant as the untreated surface; subjecting the treated surface of the article to conditions that produce wear of the surface; and observing the worn surface to determine whether there is a change in appearance indicative of wear of more than the preselected amount.

In applying the present invention, the article substrate is formed to essentially its final shape and dimensions. Then the surface is treated so that the visual appearance of the surface changes when the surface has been worn to a preselected extent. In the preferred approach, ions such as neon, nitrogen, titanium, carbon, or oxygen are implanted to the preselected depth into the surface of the article. The ions cause the visual color of the surface of the article to be different to the implanted depth. For example, if titanium and nitrogen are implanted into the surface of a material, the resulting titanium nitride has a distinctive gold color to the depth of mutual implantation. Implantation to a depth of 0.2 micrometers provides a golden colored surface for any material removal extending to that depth or less, while the surface of material removed to a greater depth would have its normal color. An inspector or operator could determine locations in which wear (including scratches) of more than 0.2 micrometers depth had occurred on the surface by searching for areas of normal material color within the golden-colored field indicating wear of less than 0.2 micrometers.

An important and desirable consideration is that the wear resistance of the treated surface may not be less than that of the untreated surface. Otherwise, the wear measurement technique would itself reduce the wear resistance of the surface. Fortunately, introduction of particular elements by implantation or otherwise can lead in many cases to surface hardening, as with the case of titanium nitride.

The treatment may be conducted directly on the article substrate using direct ion implantation, or a coating may first be deposited on the substrate and then the coating treated by ion implantation. Although color change is the preferred method of detecting wear by this technique, other properties such as reflectance may serve this purpose.

When the preferred ion implantation technique is used, the technique has the important advantage that the preselected depth of ion implantation may be controlled quite precisely and to a range of depths. Thus, for example, in one region the ions might be implanted to a depth of 0.02 micrometer and in another region the ions might be implanted to a depth of 0.2 micrometers, to produce that variation in the permitted change in dimension before the tool was judged to be unusable. The implanted surface layers are quite thin, with the advantage that a minimal amount of surface material will be removed before the wear indication appears.

Another important advantage of using ion implantation is that the temperature of the article being implanted may be maintained near ambient temperature. If tooling is heated for deposition and then cooled, it may lose its tolerances due to relaxation of stresses or warping. The ion implantation technique used with the article substrate near ambient temperature avoids this problem. As a result, it is possible to prepare the tooling to its final shape and size prior to surface treatment, perform the surface treatment, and then place the tooling into service without further machining. Final surface machining is undesirable in any event, because it would remove metal from the wear surface.

Yet another important advantage is that the dimension of the article is not changed by the implantation procedure. In ion implantation the implanted layer resides below the surface of the material. It is not an overlay coating applied to the external surface as in plating, chemical vapor deposition, or physical vapor deposition processes. The ion implantation technique of the invention has a significant advantage over coating techniques in that the article to be treated need not be pre-machined to account for surface dimensional changes introduced by the ion implantation treatment.

Other features and advantages of the invention will be apparent from the following more detailed description of the invention, taken in conjunction with the accompanying drawings, which illustrate, by way of example, the principles of the invention.

BRIEF DESCRIPTION OF THE DRAWINGS

FIG. 1 is a schematic side elevational view of a male/female set of metalworking dies during a forming operation;

FIG. 2 is a greatly enlarged side elevational view of a portion of a die bead with an ion implanted layer;

FIG. 3 is a plan view of the die bead shown in FIG. 2, prior to wear;

DETAILED DESCRIPTION OF THE INVENTION

Figure 4:
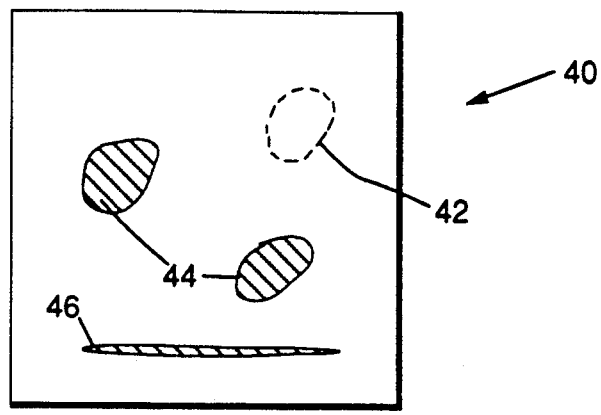
FIG. 4 is a plan view of the same region shown in FIG. 3, after wear.

Many articles are formed into desired shapes and sizes by forging, casting, molding, pressing, or stamping techniques. The articles formed, as well as the tools used to form the articles, may be either metallic or non metallic. The preferred embodiment of the present invention relates to the use of ion implantation to evaluate the extent of wear of the surface (or portions of the surface) of formed articles, or the surface of the tool used to form articles into their final shapes. Although the preferred embodiment is directed primarily toward the evaluation of the wear of tooling, and specifically the wear of dies used to form metallic articles, the invention is not so limited. The approach of the invention is much more broadly applicable to any situation where wear is occurring, as, for example, to the formation of nonmetallic articles, and the formation of articles from other tools such as foundry patterns, foundry core boxes, machine tools, cutting tools, metal working punches, etc. The term "article" includes, but is not limited to, both a piece of material formed and the tooling used to form the piece of material. "Ion implantation" includes direct ion implantation and ion beam mixing of a previously deposited coating.

In accordance with a preferred embodiment of the invention, a process for evaluating the extent of wear of manufacturing tooling comprises the steps of furnishing a substrate in the shape of a manufacturing tool and having an untreated working surface; implanting ions into a portion of the untreated working surface of the substrate to a preselected depth below the surface of the substrate, so that the appearance of the implanted region after removal by wear to a depth less than the preselected depth is different than the appearance of the treated surface at depths greater than the preselected depth, the treated surface being at least as wear resistant as the untreated surface; subjecting the treated surface of the tooling to conditions that produce wear of the surface; and observing the worn surface to determine whether there is a change in appearance indicative of wear to more than the preselected depth.

FIG. 1 illustrates a die set 20 having a male die 22 and a female die 24, at an intermediate stage of the fabrication of a thin select workpiece 26. The female die 24 has a die surface 28 of the final desired shape of the workpiece 26. The male die 22 has a corresponding shape to force the workpiece 26 into the female die 24 until the workpiece 26 reaches that final desired shape as defined by the dies.

Frictionally induced wear occurs on all of the faces of the dies 22 and 24 that contact the workpiece 26. Lubricants are typically applied to these faces to reduce friction and thence wear, but wear still occurs. After a number of forming operations with a succession of workpieces, the wear may become so large that the finished part is no longer within the required tolerances. The dies are then refurbished or scrapped, either operation being expensive.

As may be seen by inspection of FIG. 1 and as known from die forming experience, the greatest incidence of wear-induced damage typically occurs at a die bead 30 wherein the workpiece enters the female die 24. The combination of bending and frictional forces produce the most severe wear forces at the die bead 30. The present invention can therefore be beneficially utilized in conjunction with protection of the die bead 30, although it is applicable to other regions of the dies 22 and 24.

FIG. 2 illustrates the curved die bead 30 in greatly enlarged form as one portion of the die to be evaluated. As the initial step of the present approach, the die bead 30 and the remaining portions of the dies 22 and 24 are furnished in their final shape and size for the forming operation. The ability to place the dies into their final form at the outset of the process is important for two reasons. First, it permits the present invention to be used in conjunction with established die structures. The present wear evaluation process does not require a redesign of the dies. Second, no expensive post-treatment machining operations are required before the die is placed into service. Final machining of the die surfaces after treatment by ion implantation or otherwise is not permitted because it would disrupt the thin treated region.

The bead 30 includes a substrate 32 formed of a die material. The substrate can be a metal or a non-metal. A treated layer 34 is at the surface of the substrate 32. The treated layer is preferably formed by implanting ions into the surface of the substrate. In a presently most preferred form, neon ($Ne^+$), nitrogen ($N^+$ or $N_2^+$), titanium ($Ti^+$) and nitrogen ($N^+$ or $N_2^+$), carbon ($C^+$), or oxygen ($O_2^+$) ions are implanted into the surface by any acceptable ion implantation approach. Examples of acceptable ion implantation techniques are direct accelerated implantation, such as described in U.S. Pat. No. 3,900,636, or plasma source ion implantation, such as described in U.S. Pat. No. 4,764,394, whose disclosures are incorporated by reference. At the conclusion of the treatment, an upper surface 38 is exposed to a wearing environment.

The energy of implantation of the ions is selected to produce a preselected depth 36 of implantation. However, energies in the 20-300 thousand electron volt (KeV) range are typical. A characteristic of ion implantation is that the depth of implantation is dependent upon the energy used, for any selected ion and substrate. Maximum implantation depths are well known from reference works in some instances, or may be determined for any new material by conducting implantation trials at different energies an determining the maximum depth of implantation by Auger, SIMS, and DEKTAK techniques. A graph of the results provides a quick-reference source for the energy required for a particular preselected maximum implantation depth, in a particular material. The total dosage may vary as necessary to achieve sufficient visual contrast in the implanted and unimplanted material, but is typically in the range of about $10^{16}$–$10^{18}$ ions per square centimeter. For any combination of implanted ion and substrate, the required total dose is readily determined by inspecting the resulting specimens to determine the minimum dosage to produce a well-delineated contrast.

As discussed previously, a characteristic of ion implantation is that the implanted layer is thin and relatively well defined in depth distribution of the implanted species. The ability to define a thin layer is important because it allows quantitative identification of wear in excess of predetermined amounts of less than about 1 micrometer. For a typical implantation process, the implanted dose profile resembles a Gaussian distribution. In such a process utilizing an implantation energy of 100 KeV, the peak penetrating of ions in materials is on the order of 0.2-0.3 micrometers with a halfwidth spread of between 0.06 and 0.07 micrometers.

As indicated, any type of ions may be used as long as the combination of ion and substrate meet three criteria in the treated region. First, the ion must be implantable in the substrate material to the required depth. The maximum depth of implantation is the preselected depth for detection of wear. Second, the treated region as may be achieved by ion implantation must have sufficient visual contrast as compared with the underlying substrate material so that the different regions may be visually discerned. This contrast can be conveniently described as "color", because some implanted regions have a different color than do the regions having no implanted ions. The contrast can also be found in other visual characteristics, such as reflectivity or shininess after wear. Third, the ion-implanted region of the substrate must be at least as wear resistant as the substrate without ion implantation. If the ion-implanted region of the substrate were less wear resistant than the substrate without ion implantation, the purpose of the technique would be subverted. A softer treated region would wear away quickly, leaving a tool with modified dimensions and no capability for evaluation of further wear.

Examples of ions and substrates that may be used to accomplish the step of treating are summarized in the following table:

| Substrate | Implanted Ions | Surface Color |
|---|---|---|
| Metal or nonmetal | $Ti^+$ and $N_2^+$ | gold |
| Titanium | $N_2^+$ | gold |
| Titanium | $O_2^+$ | blue |
| Epoxy | $Ne^+$ | yellow, black brown |
| Stainless Steel, iron | $O_2^+$ | red |
| Stainless Steel, iron | $C^+$ | dark grey |

The use of ion implantation on surfaces has been known previously, for improved corrosion and wear resistance. It has also been recognized that the ion implantation process can color the implanted surfaces. See, for example, "Coloring of Iron Surface Controlled by $Ti^+$-$O^+$ Double-Ion Implantations", by Yoshio Okabe et al., *Nuclear Instruments and Methods in Physics Research*, Vol. B7/8, pages 184-187 (1985). However, the utilization of these phenomena in measurement of wear resistance has not been previously known.

After the treatment for wear evaluation, as by ion implantation, the tool or other article is placed into service, preferably without any further machining or modification of the tooling surface. Machining of the tooling surface would disrupt the treated layer. Treatment by ion implantation is a particularly good approach to this end, because the substrate may be maintained at near-ambient temperature during the ion implantation treatment. Other treatments such as chemical vapor deposition, plasma enhanced chemical vapor deposition, physical vapor deposition, and electrodeposition typically require that the substrate be heated to promote deposition and/or diffusion of the deposited species into the surface of the substrate. The heating of the tooling can cause it to melt or warp due to relaxation of previously introduced stresses or due to thermal expansion gradients during heating and cooling. In ion implantation, on the other hand, the substrate temperature can be maintained below 50° C. during ion implantation, resulting in little or no distortion of the tooling during the treatment.

During service, the tooling is subjected to wearing conditions of different types, such as simple friction, particle-impingement fracture, frictionally induced heating and cooling, corrosion under wearing conditions, etc. A virtue of the present approach is that its operability is not restricted to any particular type or types of wearing conditions. The only requirement of "wear", as used herein, is that material is removed from the wear surface.

FIGS. 3 and 4 schematically depict in plan view of an article 40, such as the bead 30 discussed previously, that has been treated (FIG. 3) and then subjected to wear (FIG. 4). The original treated surface is generally uniform, as shown in FIG. 3. Wear is usually local to some extent, due to various local accelerating factors, so that failure by wear usually is first manifested in isolated regions. After wear, there may be worn regions of several types. As illustrated in FIG. 4, a first type of worn region 42 experiences wear but not to the degree that material is removed below the preselected depth 36 of the treated region. A second type of worn region 44 is similar to the region 42, except that substrate material is removed to a depth greater than the preselected treatment depth 36. A third type of worn region 46 is similar to the region 44, except that it is produced by some highly directional cause such as a deep scratch.

The extent of wear on the article 40 is quickly evaluated by visual observation. In a plan view inspection prior to wear such as shown in FIG. 3, the surface of the article 40 has a uniform appearance indicated by a lack of shading. In a plan view inspection after wear such as shown in FIG. 4, regions 42 with some degree of wear less than the preselected amount (equal to the implantation depth 36) will have substantially the same color as the remainder of the surface, which color is indicative of the implanted region. Regions such as 44 and 46 where the wear is greater than the preselected amount will have a different color, which color is indicative of the original substrate or unimplanted region. If no regions of different color are seen upon visual inspection, then the wear has not progressed to the preselected amount and the article may continue in service. A visual inspection can be conducted rapidly either by a press operator or by a color-differentiating automated scanner such as a television or other optical device. The inspections can be conducted every few press cycles, at little cost except for a very brief interruption in the press operation. For example, with the present approach tooling inspection is feasible every ten or hundred press cycles, rather than every 10,000 cycles as in some prior practice.

Figure 5:
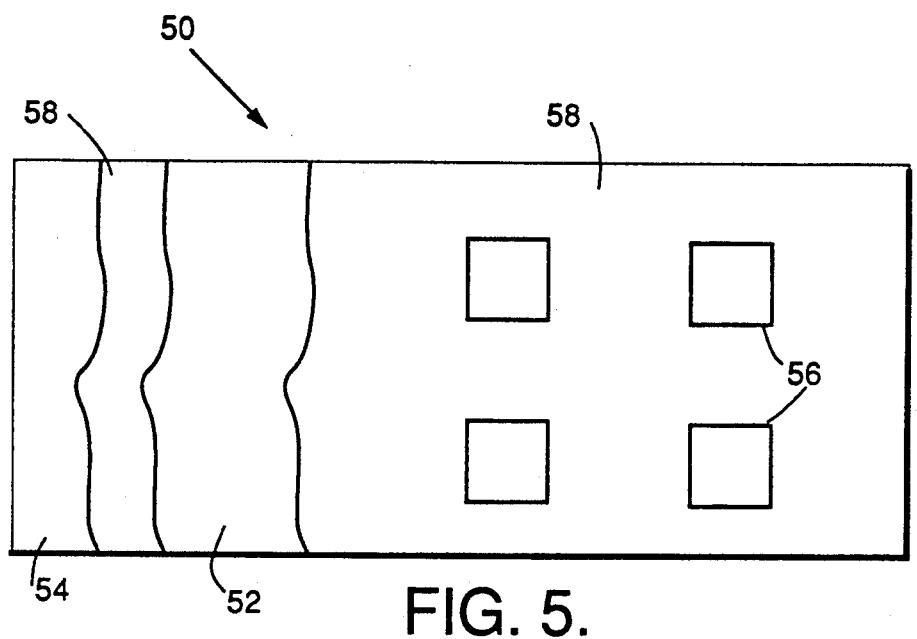
FIG. 5 is a plan view of a substrate that has been treated over a portion of its surface.

The present approach to wear evaluation has a further advantage in that the "preselected" wear indicator depth and location can be varied as desired. FIG. 5 illustrates some possible approaches. In an article 50, a region 52 is ion implanted to a first preselected depth (or, equivalently, dose), a region 54 is ion implanted to a second preselected depth, regions 56 are locally implanted, and other regions 58 are not ion implanted at all. The region 52 would exhibit a color difference after sufficient wear to penetrate the ion implanted region to the first preselected depth. The region 54 would exhibit a color difference after sufficient wear to penetrate the ion implanted region to the second preselected depth. Thus, different regions in the article 50 could be made to indicate wear beyond an acceptable amount by varying the depth of the ion implantation to correspond to the acceptable amount. In other regions, limited patches such as the regions 56 of ion implanted indicator material might be preferred, particularly at critical locations. Different patches could be implanted with different ions or to different depths, to provide indicators of progressive wear.

Some substrate materials are not suitable for direct ion implantation or other wear-indicator treatment, but another approach within the scope of the invention permits the present technique to be used. For example, a desirable short-term die tooling material is an epoxy. The epoxy is formed into a die shape, and heated to cure it. The cured material is machined to form a die surface. Ion implantation directly into the surface of this material to harden and color the surface is possible, but another approach is preferred.

Figure 6:
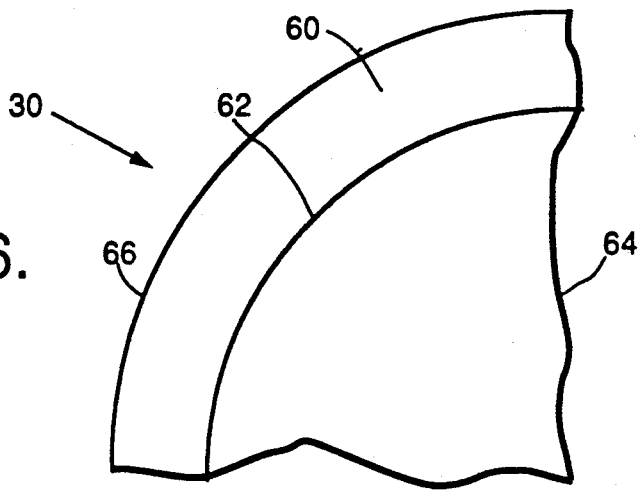
FIG. 6 is a greatly enlarged side elevational view similar to FIG. 2, with an ion implanted coating on the substrate.

This alternative approach is illustrated in FIG. 6. A thin coating 60, which is typically less than about 0.2 micrometers thick, of a silicon-containing organic material is placed onto the surface 62 of a substrate 64, and this coating is implanted with ions to mix the coating and the substrate 64 and to transform the organic material to a coating that is primarily silicon carbide. This treatment process of applying a coating and then implanting ions into the coating to alter its structure is variously termed ion beam mixing, ion beam enhanced deposition (IBED), or ion beam assisted deposition (IBAD).

An acceptable organic coating material is poly (dimethylsilane-co-methylphenylsilane) in a thickness as required for the preselected wear-indicator depth. The coating is ion implanted with neon ions with an energy required to establish the required preselected depth. The implanted coating is black or green/yellow in color, while the underlying surface is grey. An upper surface 66 if the coating 60 becomes the surface from which wear is measured. In this case, the tooling may be initially machined slightly undersized, with the coating 60 layer providing a buildup to the required final dimension. In most cases, however, the thickness so the coating 60 is so small, less than one micrometer, that the tooling may be machined to its final size within normal tolerances.

In a variation of this approach of coating the surface and thereafter implanting ions into the coating, the coating may be metallic. For example, coating a metallic surface with chromium and then ion implanting nitrogen into the coating produces a coating with a blue/purple color. Coating a metallic surface with titanium and then ion implanting nitrogen produces a gold color.

The following examples are intended to illustrate aspects of the invention, and should not be taken as limiting the invention in any respect.

EXAMPLE 1

Two groups of specimens of a zinc-based tooling material were prepared. The first group was coated with poly (dimethylsilane-co-methylphenylsilane), and ion implanted to a preselected wear depth of 0.2 micrometers with neon ions. The second group was left uncoated, and ion implanted to a depth of 0.2 micrometers with atomic nitrogen ions. The implantation conditions were 270 KeV energy and a dose of $10^{15}$ ions per square centimeter for neon ions, and 100 KeV energy and a dose of $10^{18}$ ions per square centimeter for nitrogen ions. Implantation caused the surface to turn dark grey for nitrogen ion implantation and blackish for neon ion implantation.

Specimens were wear treated in a block-on-ring apparatus and inspected. The rate of wear was significantly reduced due to ion implantation. Regions of wear were readily observed visually by a change in the color or reflectivity of the surface in those regions. Regions that wore to a depth greater than the preselected 0.2 micrometer depth showed the light silver color of the substrate to visual inspection, rather than the initial color produced by the implantation.

EXAMPLE 2

Example 1 was repeated, except that the substrate was epoxy that was formed into a die bead shape. The surface of one of the specimens was coated with a layer about 0.2 micrometers thick of poly (dimethylsilane-co-methylphenylsilane). The surface was then ion implanted with neon ions at an energy of about 270 KeV and a dose of about $4 \times 10^{14}$ per square centimeter. The ion implanted region was green/yellow in color, while the substrate was grey in color.

The treated specimen and an untreated specimen were wear tested by drawing sheet metal over the surface. A delay in the onset of surface wear was observed in the specimen which had been treated in accordance with the invention, as compared with the untreated specimen. Regions that wore through the preselected coating thickness showed the grey color of the substrate to visual examination, rather than the green/yellow color of the implanted region.

EXAMPLE 3

Nitrogen ions were implanted into titanium metal as a substrate, causing its surface to turn gold due to the formation of titanium nitride. The specimen was then ready for use in wear evaluation.

The approach of the invention thus provides an approach for evaluating the wear performance of die tooling and other articles with minimal cost. Although particular embodiments of the invention have been described in detail for purposes of illustration, various modifications may be made without departing from the spirit and scope of the invention. Accordingly, the invention is not to be limited except as by the appended claims.

What is claimed is:

1. A process for evaluating the extent of wear of manufacturing tooling, comprising the steps of:
   furnishing a substrate in the shape of a manufacturing tool and having an untreated working surface;
   treating at least a portion of the untreated working surface of the substrate with an ion treatment so that the appearance of the treated surface after wear of more than a preselected amount is altered as compared with the appearance of the treated surface that is not worn by more than the preselected amount, the treated surface being at least as wear resistant as the untreated surface, the treated surface not being machined after the step of treating and before being used as tooling;
   subjecting the treated surface of the tooling to conditions that produce wear of the surface; and
   observing the worn surface to determine whether there is a change in appearance indicative of wear of more than the preselected amount.

2. The process of claim 1, wherein the step of observing includes the step of
   determining color variations in said ion treated surface.

3. The process of claim 1, wherein the step of observing includes the step of
   determining reflectivity variations in the surface.

4. The process of claim 1, wherein the step of treating includes the step of
   implanting into the surface ions selected from the group consisting of neon, nitrogen, titanium, carbon, and oxygen.

5. The process of claim 1, wherein the step of treating includes the steps of
   depositing a coating onto the surface; and
   implanting ions into the coating.

6. A tool evaluated by the process of claim 1.

7. A process for evaluating the extent of wear of manufacturing tooling, comprising the steps of:
   furnishing a substrate in the shape of a manufacturing tool and having an untreated working surface;
   treating at least a portion of the untreated working surface of the substrate so that the appearance of the treated surface after wear of more than a preselected amount is altered as compared with the appearance of the treated surface that is not worn by more than the preselected amount, the treated surface being at least as wear resistant as the untreated surface, the treated surface not being machined after the step of treating and before being used as tooling;
   subjecting the treated surface of the tooling to conditions that produce wear of the surface; and
   observing the worn surface to determine whether there is a change in appearance indicative of wear of more than the preselected amount,
   wherein the step of treating includes the step of implanting ions into the surface.

8. A process for evaluating the extent of wear of manufacturing tooling, comprising the steps of:
   furnishing a substrate in the shape of a manufacturing tool and having an untreated working surface;
   implanting ions into a portion of the untreated working surface of the substrate to a preselected depth below the surface of the substrate, so that the appearance of the implanted region after removal by wear to a depth less than the preselected depth is different than the appearance of the treated surface at depths greater than the preselected depth, the treated surface being at least as wear resistant as the untreated surface;
   subjecting the treated surface of the tooling to conditions that produce wear of the surface; and
   observing the worn surface to determine whether there is a change in appearance indicative of wear to more than the preselected depth.

9. The process of claim 8, wherein the treated surface is not machined after the step of implanting and before the step of subjecting.

10. The process of claim 8, wherein the implanted ions are selected from the group consisting of neon, nitrogen, titanium, carbon, and oxygen.

11. The process of claim 8, including the additional step, after the step of furnishing and before the step of implanting, of
    depositing a coating onto the surface, the surface of the coating becoming the untreated surface.

12. A tool evaluated by the process of claim 8.

13. A process for evaluating the extent of wear of a selected article, comprising the steps of:
    furnishing a substrate in the shape of the selected article and having an untreated working surface;

treating at least a portion of the untreated working surface of the substrate with an ion treatment so that the appearance of the treated surface after wear of more than a preselected amount is altered as compared with the appearance of the treated surface that is not worn by more than the preselected amount, the treated surface being at least as wear resistant as the untreated surface;

subjecting the treated surface of the article to conditions that produce wear of the surface; and observing the worn surface to determine whether there is a change in appearance indicative of wear of more than the preselected amount.

14. The process of claim 13, wherein the article is a tool for use in a manufacturing process.

15. The process of claim 13, wherein the step of observing includes the step of
determining color variations in said ion treated surface.

16. The process of claim 13, wherein the step of treating includes the step of
implanting into the surface ions selected from the group consisting of neon, nitrogen, titanium, carbon, and oxygen.

17. The process of claim 13, wherein the wear resistance of the treated surface is greater than the wear resistance of the untreated surface.

18. An article evaluated by the process of claim 13.

19. A process for evaluating the extent of wear of a selected article, comprising the steps of:
furnishing a substrate in the shape of the selected article and having an untreated working surface;
treating at least a portion of the untreated working surface of the substrate so that the appearance of the treated surface after wear of more than a preselected amount is altered as compared with the appearance of the treated surface that is not worn by more than the preselected amount, the treated surface being at least as wear resistant as the untreated surface;
subjecting the treated surface of the tooling to conditions that produce wear of the surface; and
observing the worn surface to determine whether there is a change in appearance indicative of wear of more than the preselected amount,
wherein the step of treating includes the step of implanting ions into the surface.

20. A process for evaluation the extent of wear of a selected article, comprising the steps of:
furnishing a substrate in the shape of the selected article and having an untreated working surface;
treating at least a portion of the untreated working surface of the substrate so that the appearance of the treated surface after wear of more than a preselected amount is altered as compared with the appearance of the treated surface that is not worn by more than the preselected amount, the treated surface being at least as wear resistant as the untreated surface;
subjecting the treated surface of the tooling to conditions that produce wear of the surface; and
observing the worn surface to determine whether there is a change in appearance indicative of wear of more than the preselected amount; and
wherein the step of treating includes the step of determining reflectivity variations in the surface.

* * * * *